United States Patent [19]
Kobayashi et al.

[11] Patent Number: 6,090,036
[45] Date of Patent: Jul. 18, 2000

[54] HUMIDIFYING MECHANISM FOR INCUBATOR

[75] Inventors: Shinichi Kobayashi; Kazuo Matubara, both of Tokyo, Japan

[73] Assignee: Atom Medical Corporation, Tokyo, Japan

[21] Appl. No.: 09/150,538

[22] Filed: Sep. 9, 1998

[30] Foreign Application Priority Data

Sep. 9, 1997 [JP] Japan .................................. 9-260920

[51] Int. Cl.[7] .................................................. A61G 11/00
[52] U.S. Cl. ............................................................ 600/22
[58] Field of Search ............................ 600/22, 21; 5/603,
5/655; 165/60; 261/142, 153, 156, 149,
119.1; 55/95, 96

[56] References Cited

U.S. PATENT DOCUMENTS

| | | | |
|---|---|---|---|
| 4,796,605 | 1/1989 | Sasaki et al. | 600/22 |
| 5,242,375 | 9/1993 | McDonough | 600/22 |
| 5,336,156 | 8/1994 | Miller et al. | 600/22 |
| 5,616,115 | 4/1997 | Gloyd et al. | 600/22 |
| 5,792,041 | 8/1998 | Kobayashi et al. | 600/22 |

*Primary Examiner*—Samuel G. Gilbert
*Attorney, Agent, or Firm*—Hopgood, Calimafde, Kalil & Judlowe

[57] ABSTRACT

In an incubator, only water supplied from a water reservoir to a heating portion is heated. Even if the number of times of water replenishment is small, water vapor can be kept generated over a long period of time, while generation of the water vapor can be started shortly after the start of heating. In addition, since the water reservoir and heating portion that are connected to each other can be detached from and mounted on a support, both the water reservoir and the heating portion can be completely disconnected from the support. Therefore, both the water reservoir and the heating portion can be cleaned easily, facilitating use as well as maintenance.

8 Claims, 5 Drawing Sheets

HUMIDIFYING MECHANISM FOR INCUBATOR

BACKGROUND OF THE INVENTION

1. Field of the Invention

The present invention relates to an incubator in which water vapor to be supplied to a newborn baby container is generated by heating water.

2. Description of the Related Art

An incubator is used to keep a newborn baby having a particularly low vital force, e.g., an immature or premature baby, in isolation from the outer world and to raise the baby in an optimum atmosphere. Air in the room where the incubator is installed is cleaned and taken in by the incubator. Moreover, the temperature, the humidity, the oxygen concentration, and the like of the intake air are controlled to the optimum values, and the controlled air is supplied to the container.

In control of the humidity of the gas to be supplied to the container, a method of generating water vapor by heating water and controlling the mixing ratio of the water vapor and the gas, whose temperature, oxygen concentration, and the like are controlled, is often employed. Accordingly, an incubator employing this method must have a humidifying mechanism that generates water vapor by heating water.

As one related art of such an incubator, one is known which has a heating portion fixed to the main body of the incubator, and a water reservoir connected to the heating portion through a flexible tube and supported by the support of the main body. While being connected to the heating portion through the tube, the water reservoir is disconnected from the support, and the water reservoir is replenished with water. Water supplied from the water reservoir through the tube is heated by the heating portion, thereby generating water vapor.

If a gap is formed between the water vapor blowing portion of the heating portion and the main body and the like of the incubator, not all the water vapor blown from the water vapor blowing portion is supplied to the container. The water vapor may partly leak to, e.g., an oxygen concentration controller, to cause it to operate erroneously or to corrode it. For this reason, in the related art described above, the heating portion is fixed to the main body of the incubator probably in order to prevent formation of a gap between the water vapor blowing portion of the heating portion and the main body and the like of the incubator.

Since the heating portion and water reservoir of the humidifying mechanism come into direct contact with water, various germs may easily proliferate in them or boiler scale may be easily deposited on them. In the incubator of the related art described above, however, the heating portion cannot be disconnected from the main body at all, and the water reservoir cannot be sufficiently disconnected from the support as it is kept connected to the heating portion through the tube. For these reasons, in the incubator of the related art described above, the heating portion is difficult to clean, and the water reservoir is not easy to clean, either, making it difficult to easily maintain the incubator.

SUMMARY OF THE INVENTION

It is, therefore, an object of the present invention to provide an incubator in which both the water reservoir and heating portion which are used for generating water vapor to be supplied to the newborn baby container can be cleaned easily, facilitating use and maintenance.

In an incubator according to the present invention, water stored in the water reservoir is not entirely heated, but only water supplied from the water reservoir to the heating portion is heated. Even if the amount of stored water is large, the amount of water to be heated can be small. Even if the number of times of water replenishment is small, water vapor can be kept generated over a long period of time, while generation of the water vapor can be started shortly after the start of heating. In addition, since the water reservoir and heating portion that are connected to each other can be detached from and mounted on the support, both the water reservoir and the heating portion can be completely disconnected from the support. Therefore, both the water reservoir and the heating portion can be cleaned easily, facilitating use and maintenance.

In a preferred incubator according to the present invention, the water reservoir and the heating portion can be detached from and mounted on the support. Despite that, while the heating portion is supported by the support, the water vapor blowing portion of the heating portion is elastically pressed against the wall surface around an opening communicating with the container, so water vapor generated by the heating portion does not leak outside the container. As a result, portions other than the container will not operate erroneously or may be corroded, and a high reliability is ensured.

In a preferred incubator according to the present invention, the bottom surface of the water reservoir is located deeper than the bottom surface of the heating portion. Even if water runs out in the heating portion along with generation of water vapor, non-heated water is always stored in the water reservoir. Therefore, during heating with the heating portion or immediately after stopping heating, even when the water reservoir and the heating portion are disconnected from the support in order to, e.g., replenish the water reservoir with water, the heating portion can be cooled quickly by tilting the water reservoir and the heating portion to supply water from the water reservoir to the heating portion. As a result, high safety during use is ensured.

In a preferred incubator according to the present invention, a water supply port communicating with the water reservoir is formed in the recess of the lid of the water reservoir. When water is supplied to this recess, the water reservoir can be replenished with water while the water reservoir is kept closed with the lid. In addition, since the water supply port is formed in the recess of the lid, whether the water reservoir is filled with water can be confirmed, with the lid being kept placed on the water reservoir, by checking that water no longer drops from the recess into the water reservoir. As a result, the water reservoir can be easily replenished with water, further facilitating use.

DETAILED DESCRIPTION OF THE PREFERRED EMBODIMENTS

Figure 1:
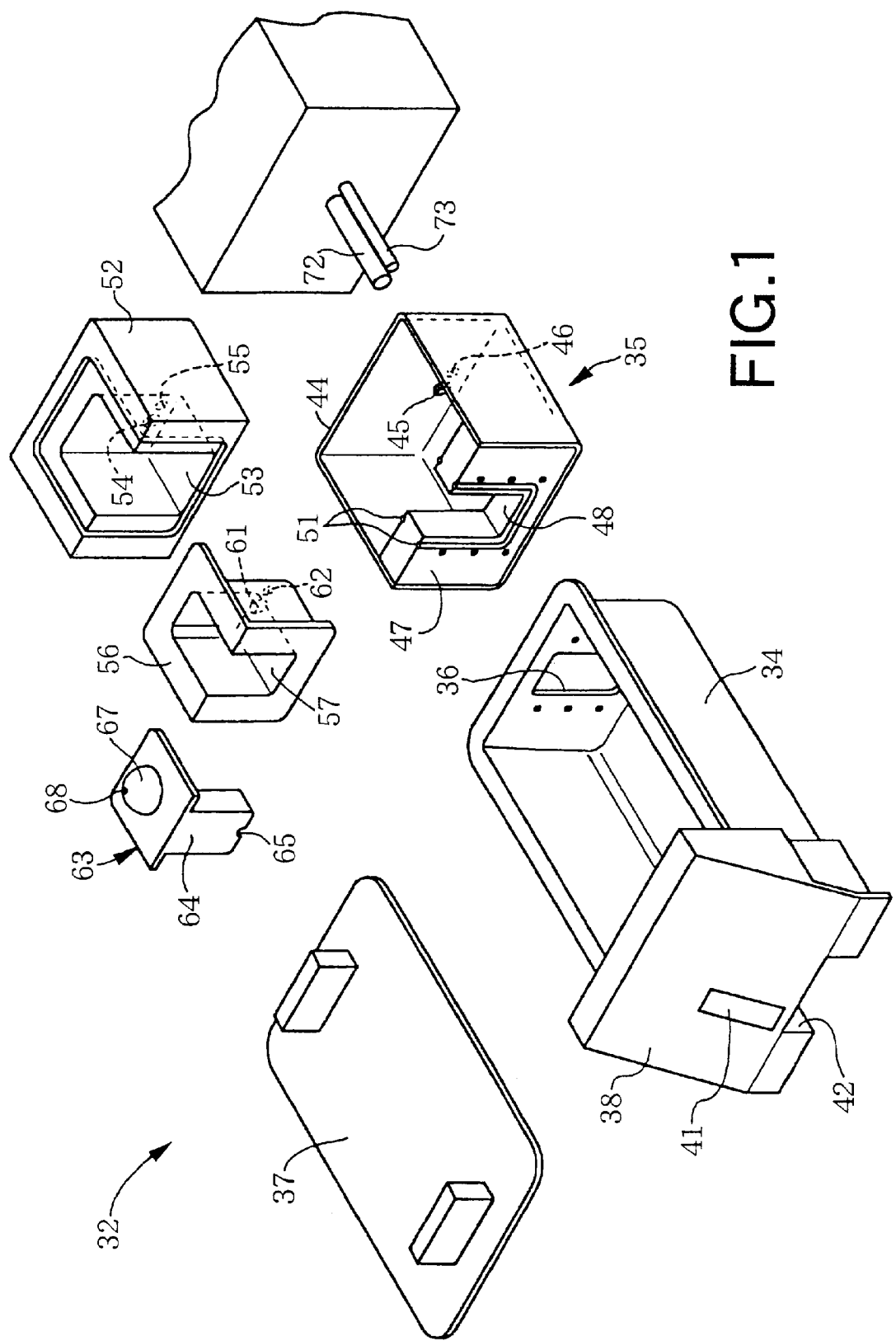
FIG. 1 is an exploded perspective view of a humidifying mechanism in the first embodiment of the present invention.

The first and second embodiments of the present invention will be described with reference to FIGS. 1 to 7. FIGS. 1 to 4 show the first embodiment. As shown in FIG. 4, in an incubator 11 of the first embodiment, an upper surface 13 of a main body 12 is covered with a transparent hood 14, and the interior of the hood 14 forms a newborn baby container 15.

The hood 14 is formed with a door (not shown) or the like. Treatment and the like for the newborn baby can be performed through this door or the like. An opening 16 is formed in the upper surface 13, and a heater 17 or the like for heating a gas is arranged in the opening 16. A plate 18 is fitted in the opening 16. In the plate 18, an opening 21 is formed at a portion near the heater 17, and an opening 22 is formed near one side surface of the main body 12.

An opening 23 different from the opening 16 is also formed in the upper surface 13. A substantially rectangular plate 24 is fitted on the upper surface 13, and notches 25 to 28 are formed in the four sides of the plate 24. A mat frame (not shown) is arranged on the plate 24, and a mat (not shown) or the like for the newborn baby to be laid on it is placed on the mat frame.

In this incubator 11, the oxygen concentration and the like of air or the like taken in through the rear surface or the like of the main body 12 are controlled to the optimum values, and the temperature of this gas is controlled to the optimum value by the heater 17. This controlled gas 31 is blown into the space between the upper surface 13 and plate 24 in a predetermined amount through the opening 21. Water vapor 33 generated by a humidifying mechanism 32 is blown into the space between the upper surface 13 and plate 24 in a predetermined amount through the opening 23.

The gas 31 and water vapor 33 are mixed with each other, and the mixture is blown to the container 15 through the notches 25 to 27. The gas 31 and water vapor 33 blown to the container 15 circulate in the container 15 and are drawn into the opening 16 through the notch 28 and opening 22. The gas 31 and water vapor 33 drawn into the opening 16 are controlled in the above manner together with the air taken in through the rear surface or the like of the main body 12, and are blown out from the opening 21 again as a fresh gas 31.

Figure 2:
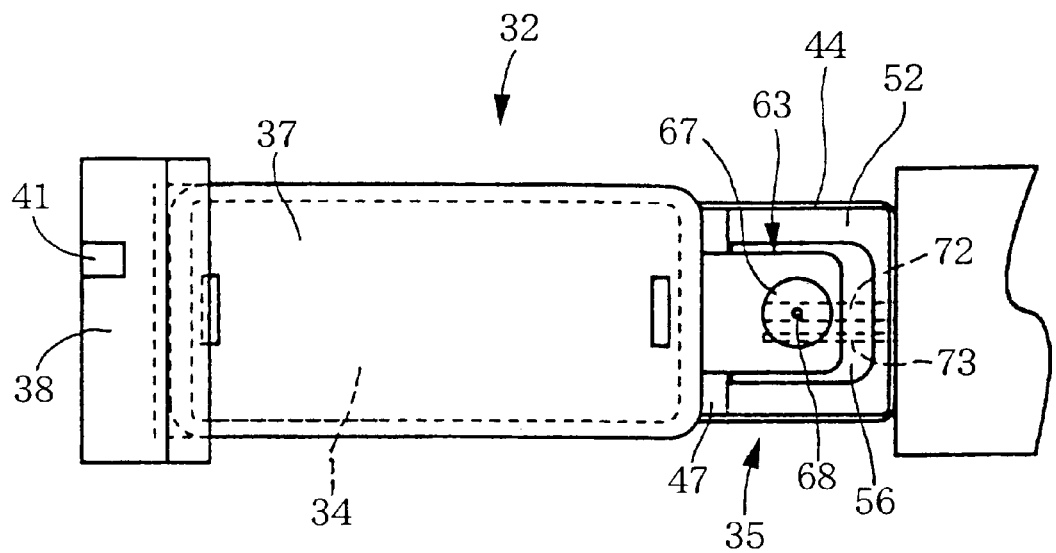
FIG. 2 is a plan view of the humidifying mechanism in the first embodiment.
Figure 3:
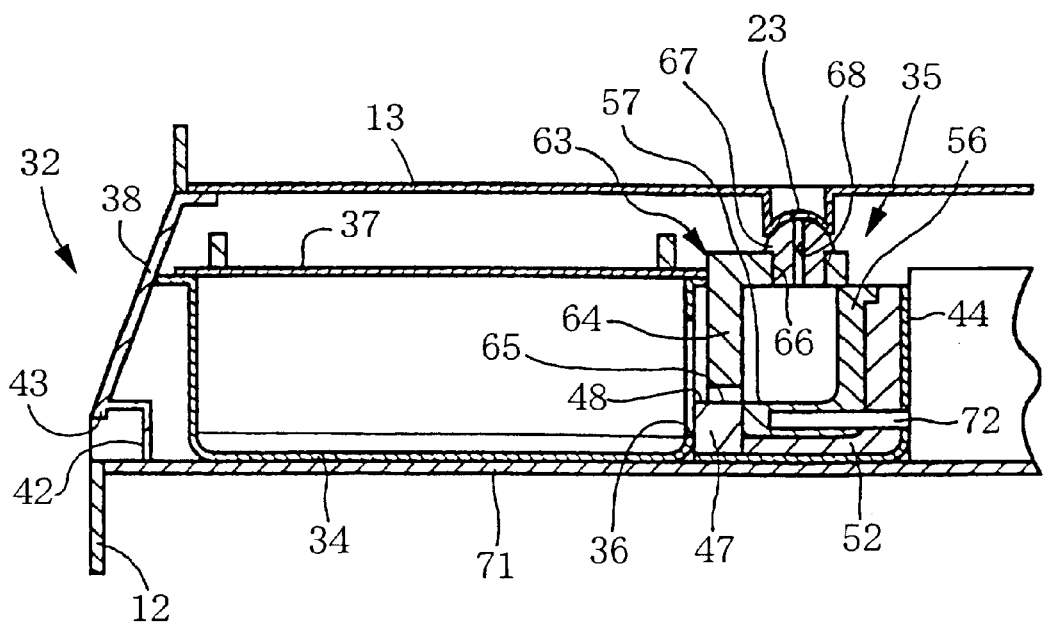
FIG. 3 is a side sectional view of the humidifying mechanism in the first embodiment.
Figure 4:
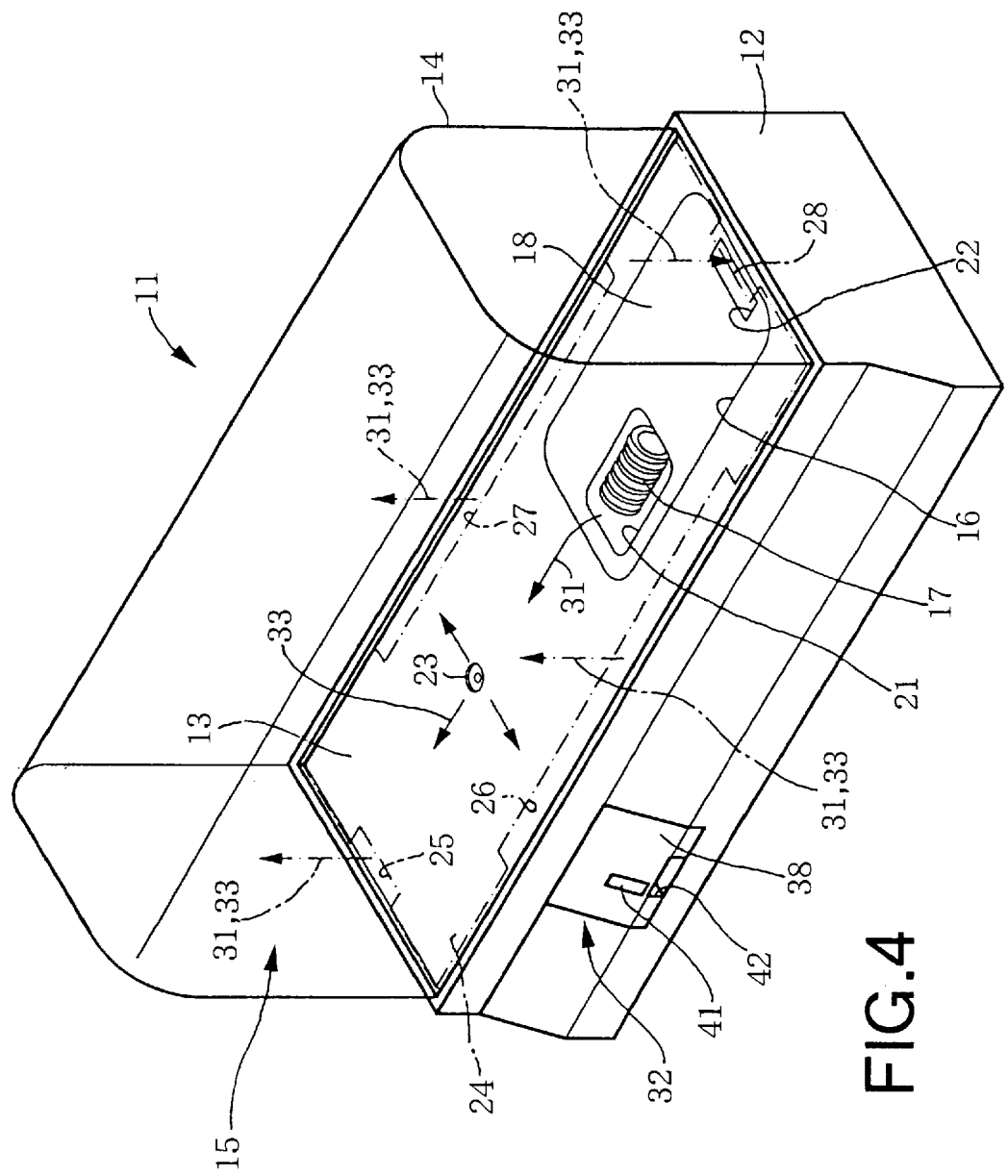
FIG. 4 is a perspective view of an incubator according to the first embodiment.

FIGS. 1 to 3 show the humidifying mechanism 32. The humidifying mechanism 32 has a water reservoir 34 and a heating portion 35 that are connected to each other with screws or the like. The water reservoir 34 is a water tank made of a synthetic resin. In the water reservoir 34, a side surface close to the heating portion 35 is formed with an opening 36. The water reservoir 34 has a lid 37.

The water reservoir 34 is connected to a front surface 38 forming part of the front surface of the main body 12. A water level indicator 41 through which the operator can see the water level of the water reservoir 34 is arranged on the front surface 38. In the front surface 38, a portion below the water level indicator 41 is formed with a recess 42. A hanging portion 43 that closes the upper end portion of the recess 42 is provided to the front surface 38.

The heating portion 35 has a frame 44 made of a polyamide-based heat-resistant synthetic resin or the like. In the frame 44, a side surface opposite to the water reservoir 34 has two through holes 45 and 46. In the frame 44, a side surface close to the water reservoir 34 is formed of a heat-insulating wall 47 made of bakelite. In the heat-insulating wall 47, a portion substantially corresponding to the opening 36 forms a notch 48. Packing rings 51 surrounding the notch 48 are fitted on the two surfaces of the heat-insulating wall 47.

A heat-insulating member 52 is fitted in the frame 44. A recess 53 is formed in the heat-insulating member 52. Through holes 54 and 55 respectively coaxial with the through holes 45 and 46 and communicating with the recess 53 are formed in the heat-insulating member 52. A metal body 56 made of aluminum or the like is fitted in the recess 53. A recess 57 substantially corresponding to the notch 48 is formed in the metal body 56. Holes 61 and 62 respectively coaxial with the through holes 54 and 55 are formed in the bottom of the metal body 56.

The metal body 56 has a lid 63 made of a heat-resistant, water vapor-resistant synthetic rubber, and a closing portion 64 which is to be fitted in the notch 48 to close most of the notch 48 is integrally formed with the lid 63. Note that a groove 65 having a small sectional area is formed in the lower end of the closing portion 64, and the notch 48 is not closed at this groove 65 portion.

A through hole 66 is formed in the lid 63, and a water vapor blowing portion 67 made of a water vapor-resistant synthetic rubber is fitted in the through hole 66. The upper half of the water vapor blowing portion 67 is hemispherical, and this hemispherical portion projects upward from the lid 63. A through hole 68 coaxial with the water vapor blowing portion 67 and communicating with the recess 57 is formed in the water vapor blowing portion 67. In the upper surface 13, a portion near the opening 23 forms a spherical shell that is fitted with the vicinity of the top of the water vapor blowing portion 67.

A support 71 is formed on the main body 12. The humidifying mechanism 32 can be inserted into and pulled out from the support 71. Hence, the support 71 serves as a receptacle capable of detachably supporting the humidifying mechanism 32. A cartridge heater 72 and an over-temperature sensor 73 project deep from the side surface of the support 71.

To generate the water vapor 33 with the humidifying mechanism 32 having the above arrangement, first, water is poured to the water reservoir 34. Even when water is not poured into the recess 57 of the metal body 56 or the lid 63 is placed on the metal body 56, water is supplied from the water reservoir 34 into the recess 57 through the opening 36, the notch 48, and the groove 65. The lid 37 is placed on the water reservoir 34, and the humidifying mechanism 32 is inserted into the support 71.

Then, the cartridge heater 72 is inserted into the hole 61 through the through holes 45 and 54, and simultaneously the over-temperature sensor 73 is inserted into the hole 62 through the through holes 46 and 55. A portion near the top of the water vapor blowing portion 67 made of the water vapor-resistant synthetic rubber is fitted on the spherical shell of the upper surface 13 near the opening 23, and is elastically pressed against it, thereby positioning the humidifying mechanism 32.

Upon operation of an appropriate switch (not shown) or actuation of a sensor (not shown) that detects insertion of the humidifying mechanism 32 into the support 71, the cartridge heater 72 is actuated. When the cartridge heater 72 is actuated, the metal body 56 is heated to heat water in the recess 57 thereafter, thereby generating the water vapor 33.

Since the portion of the water vapor blowing portion 67 near its top is elastically pressed against the spherical shell near the opening 23, the water vapor 33 generated in the recess 57 flows through the through hole 68 and opening 23, is blown into only the space between the upper surface 13 and plate 24, and is blown into the container 15 through the notches 25 to 27. Namely, after flowing through the through hole 68, no water vapor 33 leaks from the gap between the water vapor blowing portion 67 and the upper surface 13 without flowing through the opening 23, so the oxygen concentration controller (not shown) and the like may not operate erroneously or may not be corroded.

Despite the large capacity of the water reservoir 34 of 1.3 liters, the capacity of the recess 57 is as small as 50 milliliters. In addition, the metal body 56 is surrounded by the heat-insulating wall 47 and heat-insulating member 52, and water convection does not easily occur between the water reservoir 34 and recess 57 due to the small sectional area of the groove 65 formed in the closing portion 64. Therefore, the cartridge heater 72 heats mostly the metal body 56 and water in the recess 57 of the metal body 56.

For this reason, generation of the water vapor 33 can be started shortly after the start of heating with the cartridge heater 72, facilitating use. When the temperature of the metal body 56 becomes equal to or higher than a predetermined value, the over-temperature sensor 73 is actuated to stop actuation of the cartridge heater 72. Accordingly, the metal body 56 and the like will not be overheated, and the high-temperature water vapor 33 will not be blown into the container 15.

Assume that it is to be detected, through observation with the water level indicator 41, that the water level of the water reservoir 34 is equal to or lower than a predetermined level, and that the water reservoir 34 is to be replenished with water, or that the humidifying mechanism 32 is to be cleaned. In this such a case, the operator inserts his finger into the recess 42 and holds the hanging portion 43 with his finger to pull out the front surface 38 from the support 71. Since the front surface 38, the water reservoir 34, and the heating portion 35 are connected to each other and the heating portion 35 is not fixed to the main body 12, the entire portion of the humidifying mechanism 32 can be completely disconnected from the support 71 by only pulling out the front surface 38.

In addition, as is apparent from FIGS. 1 and 2, the boundaries between the bottom surface and the side surfaces of the water reservoir 34 and the boundaries between the side surfaces of the recess 57 of the metal body 56 form curved surfaces having a particularly large radius of curvature. Accordingly, the entire portion of the humidifying mechanism 32, particularly the water reservoir 34 and the recess 57 of the metal body 56 that come into direct contact with water can be cleaned easily, facilitating maintenance.

As is apparent from FIG. 3, since the bottom surface of the water reservoir 34 is deeper than the bottom surface of the recess 57 of the metal body 56, even if water runs out in the recess 57 along with generation of the water vapor 33, non-heated water is always stored in the water reservoir 34. Therefore, even when the humidifying mechanism 32 is disconnected from the support 71 during heating with the heating portion 35 or immediately after stopping heating, the heating portion 35 can be cooled quickly by tilting the humidifying mechanism 32 to supply water from the water reservoir 34 to the recess 57, providing high safety in use.

Figure 5:
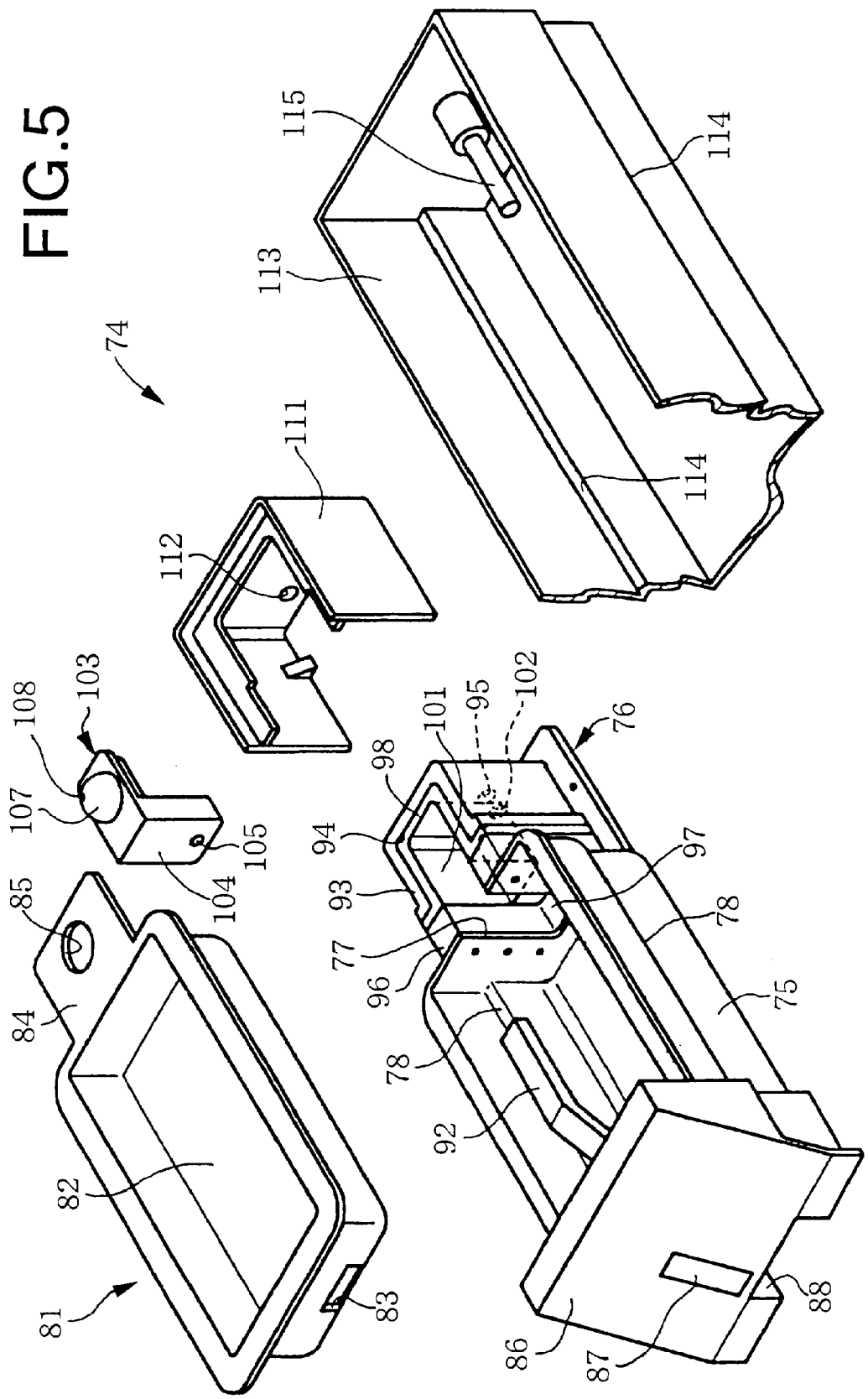
FIG. 5 is an exploded perspective view of a humidifying mechanism in the second embodiment of the present invention.
Figure 6:
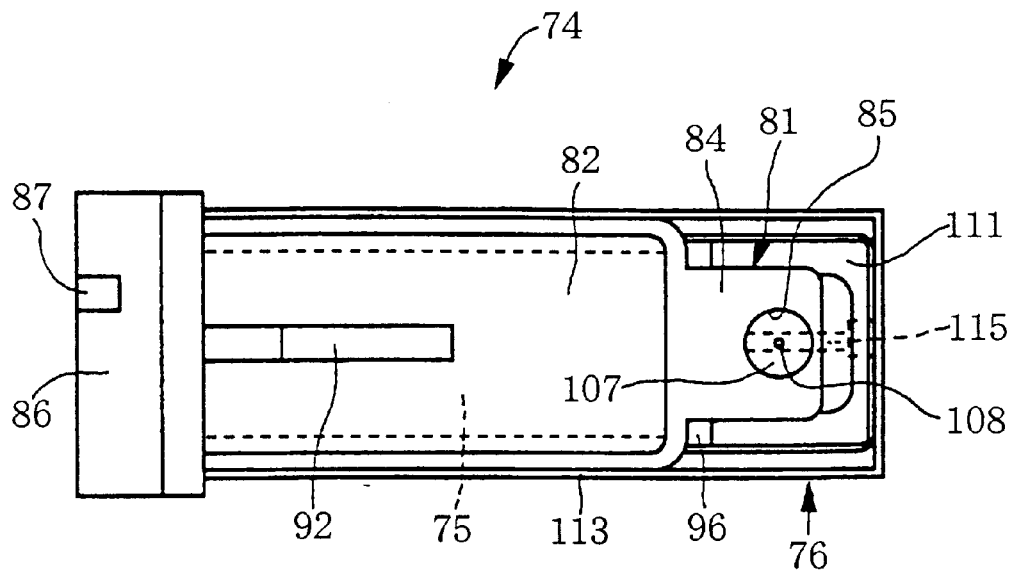
FIG. 6 is a plan view of the humidifying mechanism in the second embodiment.
Figure 7:
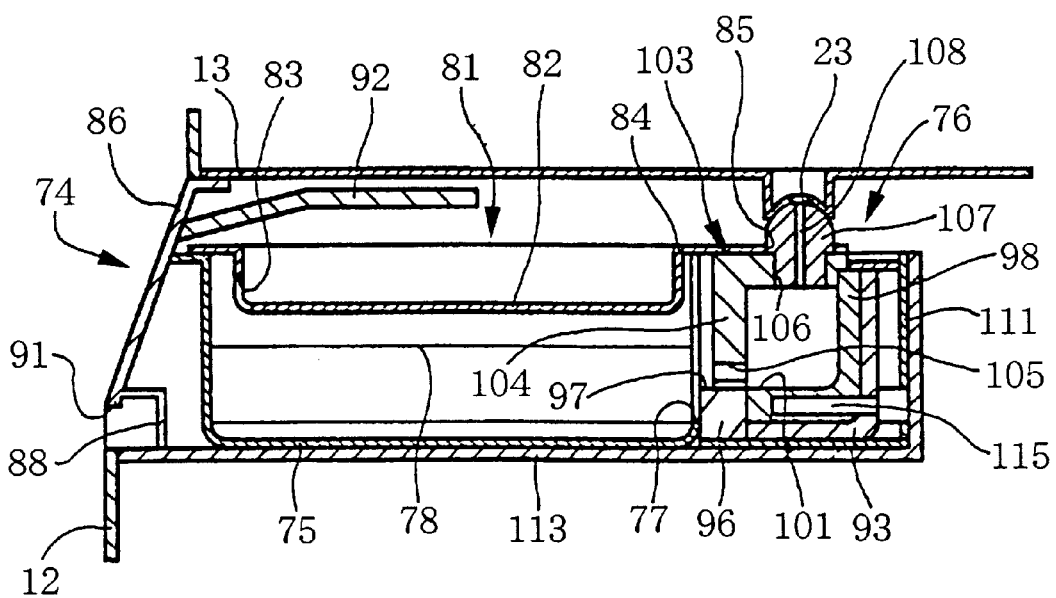
FIG. 7 is a side sectional view of the humidifying mechanism in the second embodiment.

FIGS. 5 to 7 show a humidifying mechanism in the second embodiment. Except for the humidifying mechanism, the incubator according to the second embodiment has substantially the same arrangement as that of the incubator 11 of the first embodiment shown in FIG. 4.

A humidifying mechanism 74 according to the second embodiment has a water reservoir 75 and a heating portion 76 that are connected to each other with screws or the like. The water reservoir 75 is a water tank made of a synthetic resin. In the water reservoir 75, a side surface close to the heating portion 76 has a notch 77, and a pair of side surfaces that are in contact with this side surface have steps 78, respectively.

The water reservoir 75 has a lid 81. A recess 82 is formed in substantially the entire portion of the lid 81, and a water supply port 83 is formed in one side of the bottom surface of the recess 82. In the lid 81, a side opposite to the side formed with the water supply port 83 has a projecting piece 84, and a through hole 85 is formed in the projecting piece 84.

Similar to the first embodiment, the water reservoir 75 of the second embodiment is connected to a front surface 86, and a water level indicator 87, a recess 88, and a hanging portion 91 are provided to the front surface 86. Note that a handle 92 is formed above the water reservoir 75 of the second embodiment.

The heating portion 76 has a heat-insulating member 93. The heat-insulating member 93 has a recess 94. In the heat-insulating member 93, a side surface opposite to the water reservoir 75 has a through hole 95. A heat-insulating packing 96 is disposed between the heat-insulating member 93 and water reservoir 75, and a notch 97 corresponding to the notch 77 of the water reservoir 75 is formed in the heat-insulating packing 96.

A metal body 98 made of aluminum or the like is fitted in the recess 94 of the heat-insulating member 93 and between the heat-insulating member 93 and the heat-insulating packing 96. A recess 101 substantially corresponding to the notch 97 is formed in the metal body 98. A hole 102 coaxial with the through hole 95 is formed in the bottom of the metal body 98.

The metal body 98 has a lid 103 made of a heat-resistant, water vapor-resistant synthetic rubber, and a closing portion 104 which is to be fitted in the notch 97 to close most of the notch 97 is integrally formed with the lid 103. Note that a through hole 105 having a small sectional area is formed in the lower end of the closing portion 104, and the notch 97 is not closed at this through hole 105 portion.

A through hole 106 is formed in the lid 103, and a water vapor blowing portion 107 made of a water vapor-resistant synthetic rubber is fitted in the through hole 106. The upper half of the water vapor blowing portion 107 is hemispherical, and this hemispherical portion projects upward from the lid 103. A through hole 108 coaxial with the water vapor blowing portion 107 and communicating with the recess 101 is formed in the water vapor blowing portion 107.

The metal body 98, the heat-insulating member 93, and the heat-insulating packing 96 are surrounded by a heat-insulating cover 111 made of a polyamide-based heat-resistant synthetic resin or the like, and a through hole 112 coaxial with the through hole 95 is formed in the heat-insulating cover 111.

A support 113 is formed on a main body 12. The humidifying mechanism 74 can be inserted into and pulled out from the support 113. Hence, the support 113 serves as a receptacle capable of detachably supporting the humidifying mechanism 74. Steps 114 are formed on the two side surfaces of the support 113. When inserting and pulling out the humidifying mechanism 74, the steps 114 are fitted with the steps 78 of the water reservoir 75 to guide the water reservoir 75. A heater unit 115 incorporating a control sensor projects deep from the side surface of the support 113.

With the humidifying mechanism 74 having the above arrangement, when the lid 103 is placed on the metal body 98, the lid 81 is placed on the water reservoir 75, and the water vapor blowing portion 107 is fitted in the through hole 85, the lid 81 is positioned with respect to the water reservoir 75 and the like. Since the lid 81 has the recess 82 and water supply port 83, the water reservoir 75 can be replenished with water, while the lid 81 is kept placed on the water reservoir 75, by pouring water to the recess 82.

In addition, whether the water reservoir 75 is filled with water can be confirmed, with the lid 81 being kept placed on the water reservoir 75, by checking that water no longer drops from the recess 82 into the water reservoir 75. As a result, water can be easily replenished to the water reservoir 75, facilitating use.

When water is poured to the water reservoir 75, it is supplied from the water reservoir 75 into the recess 101 of the metal body 98 through the notches 77 and 97 and the through hole 105. When the humidifying mechanism 74 is inserted into the support 113, the heater unit 115 is inserted into the hole 102 through the through holes 112 and 95. Upon operation of an appropriate switch (not shown) or actuation of a sensor (not shown) that detects insertion of the humidifying mechanism 74 into the support 113, the heater unit 115 is actuated.

The materials of the respective components of the humidifying mechanisms 32 and 74 in the first and second embodiments are not limited to those described above, and the shapes of the respective components and the like of the humidifying mechanisms 32 and 74 are not limited to those shown in the accompanying drawings.

What is claimed is:

1. A humidifying mechanism for an incubator in which water vapor to be supplied to a newborn baby container is generated by heating water, comprising:

a water reservoir for storing the water, a heating portion connected to said water reservoir through a passage having a sectional area smaller than sectional areas of said water reservoir and said heating portion to heat the water supplied from said water reservoir through said passage, and a support for detachably supporting said water reservoir and said heating portion that are connected to each other.

2. A humidifying mechanism for an incubator according to claim 1, wherein said support detachably supports said water reservoir and said heating portion, a water vapor blowing portion of said heating portion is elastically pressed against a wall surface around an opening that communicates with said container.

3. A humidifying mechanism for an incubator according to claim 1, wherein said water reservoir has a bottom surface deeper than a bottom surface of said heating portion.

4. A humidifying mechanism for an incubator according to claim 1, wherein said water reservoir has a lid which is formed with a recess at least partly, and a water supply port communicating with said water reservoir is formed in said recess.

5. An incubator in which water vapor to be supplied to a newborn baby container is generated by heating water such incubator having a water reservoir for storing the water, a heating portion connected to said water reservoir to heat the water supplied therefrom, and a support for detachably supporting said water reservoir and said heating portion that are connected to each other, wherein the improvement comprises:

connecting said heating portion and said water reservoir through a passage having a sectional area smaller than sectional areas of said water reservoir and said heating portion.

6. A humidifying mechanism for an incubator according to claim 5, wherein said support detachably supports said water reservoir and said heating portion, a water vapor blowing portion of said heating portion is elastically pressed against a wall surface around an opening that communicates with said container.

7. A humidifying mechanism for an incubator according to claim 5, wherein said water reservoir has a bottom surface deeper than a bottom surface of said heating portion.

8. A humidifying mechanism for an incubator according to claim 5, wherein said water reservoir has a lid which is formed with a recess at least partly, and a water supply port communicating with said water reservoir is formed in said recess.

\* \* \* \* \*